US011028349B2

(12) United States Patent
Ruan et al.

(10) Patent No.: US 11,028,349 B2
(45) Date of Patent: Jun. 8, 2021

(54) CLEANSING COMPOSITIONS COMPRISING A MIXTURE OF PHENOL DISINFECTANTS

(71) Applicant: Colgate-Palmolive Company, New York, NY (US)

(72) Inventors: Yang Ruan, Guangzhou (CN); Huiyan Yin, Guangzhou (CN); Eugene Hardy, Old Bridge, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 16/073,831

(22) PCT Filed: Jan. 26, 2017

(86) PCT No.: PCT/US2017/015102
§ 371 (c)(1),
(2) Date: Jul. 30, 2018

(87) PCT Pub. No.: WO2017/132356
PCT Pub. Date: Aug. 3, 2017

(65) Prior Publication Data
US 2019/0040339 A1 Feb. 7, 2019

(30) Foreign Application Priority Data
Jan. 29, 2016 (CN) .......................... 201610066396.9

(51) Int. Cl.
| C11D 1/94 | (2006.01) |
| C11D 3/48 | (2006.01) |
| A61K 8/34 | (2006.01) |
| A61Q 17/00 | (2006.01) |
| A61Q 19/10 | (2006.01) |
| C11D 3/20 | (2006.01) |
| C11D 3/24 | (2006.01) |

(52) U.S. Cl.
CPC ............... C11D 3/48 (2013.01); A61K 8/347 (2013.01); A61Q 17/005 (2013.01); A61Q 19/10 (2013.01); C11D 3/2034 (2013.01); C11D 3/2068 (2013.01); C11D 3/24 (2013.01); A61K 2800/77 (2013.01)

(58) Field of Classification Search
CPC .... C11D 1/12; C11D 1/29; C11D 1/90; C11D 3/0094; C11D 3/2079; C11D 3/33; C11D 3/48; C11D 17/0047
See application file for complete search history.

(56) References Cited

U.S. PATENT DOCUMENTS

| 5,705,532 | A | * | 1/1998 | Modak | A01N 47/44 |
| | | | | | 514/635 |
| 6,106,851 | A | | 8/2000 | Beerse et al. | |
| 6,451,333 | B1 | * | 9/2002 | Beerse | A61K 8/347 |
| | | | | | 424/401 |
| 6,525,071 | B2 | * | 2/2003 | Dyer | A01N 33/12 |
| | | | | | 514/320 |
| 6,805,874 | B1 | | 10/2004 | Lutz et al. | |
| 8,778,861 | B2 | | 7/2014 | Shi et al. | |
| 2006/0040847 | A1 | * | 2/2006 | Weibel | C11D 3/24 |
| | | | | | 510/504 |
| 2006/0115440 | A1 | * | 6/2006 | Arata | A61Q 5/02 |
| | | | | | 424/65 |
| 2008/0312327 | A1 | * | 12/2008 | Rypkema | C11D 3/2027 |
| | | | | | 514/570 |
| 2012/0322712 | A1 | * | 12/2012 | Yao | C11D 17/08 |
| | | | | | 510/159 |
| 2013/0065829 | A1 | * | 3/2013 | Day | C07K 7/06 |
| | | | | | 514/8.1 |
| 2014/0057003 | A1 | * | 2/2014 | Johnson | A47K 5/1217 |
| | | | | | 424/725 |
| 2016/0058684 | A1 | * | 3/2016 | Jiang | A61K 8/27 |
| | | | | | 514/188 |
| 2016/0143825 | A1 | * | 5/2016 | Pesaro | A61K 8/37 |
| | | | | | 424/55 |
| 2016/0362646 | A1 | * | 12/2016 | Agarkhed | C11D 3/1213 |
| 2017/0055523 | A1 | * | 3/2017 | Malchesky | C11D 17/003 |
| 2018/0042825 | A1 | * | 2/2018 | Lei | B32B 5/16 |

FOREIGN PATENT DOCUMENTS

| CN | 1265027 A | 8/2000 |
| JP | 2008-138027 A | 6/2008 |
| WO | 2010/112577 | 10/2010 |
| WO | 2015/138479 | 9/2015 |
| WO | 2015/189566 | 12/2015 |

OTHER PUBLICATIONS

International Search Report and Written Opinion of the International Searching Authority in International Application No. PCT/US2017/015102, dated Jul. 10, 2017.
Kazuo et al., 2008, "Liquid Bactericidal Detergent Composition," WPI Derwent Database AN 2008-J00125 & JP 2008-138027A.
Ash et al., 2004, "Handbook of Preservatives," Synapse Information Resources, Inc., New York, pp. 347 and 566-567.
Clariant, 2005, "Antidandruff Active Ingredient Octopirox®" URL: <http://www.essentialingredients.com/pdf/ClariantOctopiroxBrochure.pdf> published in Jun. 2005.
De Traay, 2008, "Anti-Dandruff Shampoo" Mintel GNPD AN: 866804.
Jan Dekker International, "Dekasol BL—A preservative booster for skin-care products," URL: www.in-cosmetics.com novadocuments 8296, published Mar. 21, 2015.
Ji et al., 2003, "Antibacterial Materials," Chemical Industry Press, p. 284.
Pola, 2010, "Medicated Hand Soap," Mintel GNPD AN: 1255079.
Qian, 2010, "Fine Chemicals Chemistry," Northeast University Press, pp. 243-244.

* cited by examiner

*Primary Examiner* — Charles I Boyer

(57) ABSTRACT

Described herein, are personal care compositions comprising an effective amount of an antibacterial component selected from chloroxylenol (PCMX) and o-cymene-5-on (IPMP); phenoxyethanol; piroctone olamine; and a surfactant. Methods of making and using these compositions are also described.

10 Claims, No Drawings

CLEANSING COMPOSITIONS COMPRISING A MIXTURE OF PHENOL DISINFECTANTS

CROSS-REFERENCE TO RELATED APPLICATION

This application claims the benefit of Chinese Patent Application No. 201610066396.9, filed Jan. 29, 2016, the entirety of which is hereby incorporated herein by reference.

BACKGROUND

Antibacterial soaps have become widespread over the last twenty years and are very popular with consumers. The two most common antibacterial agents used in soaps, triclosan and triclocarban, are very effective in cleansing applications, and eliminate very high quantities of bacteria on a user's skin. However, there remains a need for alternative antibacterial agents that are as effective as triclosan and triclocarban for formulation in personal hygiene products, particularly cleansing liquids and bars.

Embodiments of the present invention are designed to meet these, and other, needs.

BRIEF SUMMARY

Compositions, methods of use, and methods of production for cleansing a surface having a population of bacteria are provided herein. Safe and effective compositions having antibacterial properties are also provided. Also provided are personal care compositions that provide long-lasting antibacterial effects for the consumer.

It has been discovered that personal care compositions with antibacterial agents comprising chloroxylenol (also referred to herein as 4-chloro-3,5-dimethylphenol or PCMX), o-cymen-5-ol (also referred to herein as 4-isopropyl-3-methylphenol or IPMP), and optionally phenoxyethanol surprisingly provide highly antibacterial properties.

In a first exemplary embodiment, provided is a personal care composition comprising an antibacterial component; said antibacterial component comprising an effective amount of chloroxylenol and o-cymen-5-ol; and a surfactant.

In a second exemplary embodiment, provided is a method of cleansing a surface comprising applying the composition to a surface, for example wherein the surface has a population of bacteria; for example a skin surface.

In a third exemplary embodiment, provided is a method for preparing an antibacterial composition comprising combining an effective amount of chloroxylenol, o-cymen-5-ol, and/or optionally phenoxyethanol with at least one surfactant.

DETAILED DESCRIPTION

Unless otherwise specified, all percentages and amounts expressed herein and elsewhere in the specification should be understood to refer to percentages by weight. As used throughout, ranges are used as shorthand for describing each and every value that is within the range. Any value within the range can be selected as the terminus of the range.

As used herein, the term "cleansing bar" shall include soap bars for cleansing and personal hygienic use comprising a cleansing soap material.

As used herein, the term "cleansing liquid" shall include soap liquids for cleansing and personal hygienic use comprising a cleansing soap material.

As used herein, the term "effective amount" is intended to mean an amount that effective to produce a desired effect, for example antibacterial efficacy.

The present disclosure provides personal care compositions comprising chloroxylenol and o-cymen-5-ol, and one or more surfactants. In some embodiments, the compositions include one or more additional antibacterial agents, such as, for example, phenoxyethanol.

In one exemplary embodiment, the present disclosure provides a personal care composition (Composition 1) comprising an effective amount of an antibacterial component and a surfactant; the antibacterial component comprising chloroxylenol and o-cymen-5-ol.

The present disclosure provides additional exemplary embodiments, including:

1.1 Composition 1, wherein the chloroxylenol is present in an amount of about 0.01% to about 2.0% by weight of the composition, about 0.05% to about 1% by weight of the composition; 0.1% to about 0.8% by weight of the composition, about 0.2% to about 0.6% by weight of the composition, about 0.2% to about 0.4% by weight of the composition, or about 0.3% by weight of the composition; or about 0.5% by weight of the composition.

1.2 Any of Compositions 1 or 1.1, wherein the o-cymen-5-ol is present in an amount of about 0.001% to about 5.0% by weight of the composition, about 0.01% to about 3.0% by weight of the composition, about 0.05% to about 0.5% by weight of the composition, or about 0.1% by weight of the composition.

1.3 Any of Compositions 1 or 1.1-1.2, wherein the composition comprises about 0.2% to about 0.6% by weight of chloroxylenol and about 0.05% to about 0.5% by weight of o-cymen-5-ol.

1.4 Any of Compositions 1 or 1.1-1.3, further comprising phenoxyethanol.

1.5 Composition 1.4, wherein the phenoxyethanol is present in an amount of about 0.01% to about 5% by weight of the composition, about 0.1% to about 2% by weight of the composition, or about 1% by weight of the composition.

1.6 Composition 1.4, wherein the composition comprises about 0.01% to about 2.0% by weight of chloroxylenol, about 0.001% to about 5.0% by weight of o-cymen-5-ol, and about 0.01% to about 5.0% by weight of phenoxyethanol.

1.7 Any of Compositions 1 or 1.1-1.6, wherein the composition is in the form of a liquid soap or a bar soap.

1.8 Any of Compositions 1 or 1.1-1.7, wherein the surfactant is selected from one or more of an anionic surfactant, a non-ionic surfactant, and an amphoteric (i.e., zwitterionic) surfactant, 1.9 Any of Compositions 1 or 1.1-1.8, comprising an anionic surfactant and a zwitterionic surfactant.

1.10 Any of Compositions 1 or 1.1-1.9, wherein the composition further comprises one or more ingredients selected from among:
  (a) Humectants (e.g., glycerin, sorbitol, propylene glycol),
  (b) Fatty acids (e.g., caproic acid, caprylic acid, capric acid, lauric acid, myristic acid, palmitic acid, palmitoleic acid, stearic acid, oleic acid, linolenic acid, linoleic acid, arachidic acid, arachidonic acid),
  (c) Fatty alcohols (e.g., cetearyl alcohol, cetyl alcohol, stearyl alcohol, oleyl alcohol),
  (d) Esters of fatty acids (e.g., esters of caproic acid, caprylic acid, capric acid, lauric acid, myristic acid, palmitic acid, palmitoleic acid, stearic acid, oleic acid, linolenic acid, linoleic acid, arachidic acid, arachidonic acid, with alcohols such as glycerol, propylene glycol, sorbitan, isopropyl alcohol, caproic alcohol, capryl alcohol, capric alcohol, lauryl alcohol, myristyl alcohol, cetearyl alcohol, cetyl alcohol, palmoleyl alcohol, stearyl alcohol, oleyl alcohol, linoyl alcohol, linolenyl alcohol, arachidyl alcohol, arachidonyl alcohol) such as isopropyl myristate, capryl stearate, isopropyl olivate, cetearyl olivate, cetearyl oleate, glyceryl caprylate, glyceryl stearate citrate, and sorbitan olivate), natural and synthetic triglycerides (e.g., di- or tri-glycerides of fatty acids, such as glyceryl caprate or caprylic/capric triglyceride),
  (e) Natural fats and oils (e.g., vegetable oil, coconut oil, sesame oil, avocado oil, corn oil, castor oil, shea butter, cocoa butter, soybean oil, sunflower oil, safflower oil, olive oil and tallow),
  (f) Waxes (e.g., cetearyl wax, beeswax, carnauba wax, lanolin wax, candelilla wax, and paraffin wax),
  (g) Thickeners (e.g., silicas, xanthan gum, guar gum, agar, alginates, carrageenan, gellan gum, pectins, and modified cellulose polymers, such as hydroxycellulose, hydroxypropyl cellulose, hydroxyethyl cellulose, hydroxybutyl cellulose, hydropropyl methylcellulose, hydroxyethyl propyl cellulose),
  (h) Emulsifiers polyethylene glycol esters, fatty alcohol polyglycol ethers, fatty acid polyglycol ethers, polyglycerol fatty acid esters, sorbitol, sorbitan, and mono- and di-fatty acid esters of sorbitan),
  (i) Sunscreen actives (e.g., titanium dioxide, zinc oxide, and UV absorption inhibitors, such as octyl methoxy cinnamate, benzophenone-3, and methylene bis-benzotriazolyl tetramethyl butyl phenol),
  (j) Vitamins (e.g., vitamin A, vitamin E, esters of vitamin A or vitamin E, such as vitamin E acetate and retinyl palmitate, or pro-vitamin derivatives thereof such as, for example, vitamin E acetate.
1.11 Any of Compositions 1 or 1.1-1.10, wherein the composition is a cream, lotion or gel for the skin (e.g., face, hands, feet, etc.).
1.12 Any of Compositions 1 or 1.1-1.11, further comprising inorganic salts, brighteners, perfumes, colorants, sequestering agents, opacifiers, pearlizers, chelating agents (e.g., EDTA), or any combination thereof.
1.13 Any of Compositions 1 or 1.1-1.12, wherein the composition is a cosmetic product, cosmetic-removal product, hair care product, shaving product (e.g., creams, gels and foams), skin care product or personal cleansing product (e.g., liquid soaps, foams, gels, and lotions).
1.14 Composition 1 or any of 1.1-1.13, further comprising natural biological extracts, such as essential oils or fragrances (e.g., Amyris oil, cedarwood oil, cocoa absolute, copaiba balsam, menthe oil pays, myrrh resin, patchouli oil, vanillin, vetiver oil, aloe extract, lemon extract, orange extract, mandarin extract, and oil or extract of anise, clove, basil, aniseed, cinnamon, geranium, rose, mint, lavender, thyme, rosemary, citronella, cypress, eucalyptus, peppermint, and sandalwood).
1.15 Composition 1 or any of 1.1-1.15, further comprising water, e.g., from 5-90% water by weight of the composition, for example, 10%-80%, 15%-80%, 20%-80%, 25%-80%, 25%-75%, 30%-75%, 30%-80%, 40%-80%, 40%-70%, 50-75%, 50%-70%, 50%-65%, or 60%-70%, or 65-70%, or about 65%, or about 66%, or about 67%, or about 68%.
1.16 Composition 1 or any of 1.1-1.16, wherein the pH of the composition is from 8-14; for example, from 8.0-12.0, or from 8.0-10.0.

In a further embodiment, the present disclosure provides a personal care composition (Composition 2) comprising an effective amount of an antibacterial component; a surfactant; and phenoxyethanol; said antibacterial component comprising o-cymen-5-ol.

The present disclosure provides additional exemplary embodiments, including:
2.1 Compositions 2, wherein the o-cymen-5-ol is present in an amount of about 0.001% to about 5.0% by weight of the composition, about 0.01% to about 3.0% by weight of the composition, about 0.05% to about 0.5% by weight of the composition, or about 0.1% by weight of the composition.
2.2 Compositions 2 or 2.1, wherein the phenoxyethanol is present in an amount of about 0.01% to about 5% by weight of the composition, about 0.1% to about 2% by weight of the composition, or about 1% by weight of the composition.
2.3 Composition 2.2, wherein the composition comprises about 0.01% to about 1% by weight of o-cymen-5-ol, and about 0.01% to about 3.0% by weight of phenoxyethanol.
2.4 Any of Compositions 2 or 2.1-2.3, wherein the composition is in the form of a liquid soap or a bar soap.
2.5 Any of Compositions 2 or 2.1-2.4, wherein the surfactant is selected from one or more of an anionic surfactant, a non-ionic surfactant, and an amphoteric (i.e., zwitterionic) surfactant.
2.6 Any of Compositions 2 or 2.1-2.5, comprising an anionic surfactant and a zwitterionic surfactant.
2.7 Any of Compositions 2 or 2.1-2.6, wherein the composition further comprises one or more ingredients selected from:
  (k) Humectants (e.g., glycerin, sorbitol, propylene glycol),
  (l) Fatty acids e.g., caproic acid, caprylic acid, capric acid, lauric acid, myristic acid, palmitic acid, palmitoleic acid, stearic acid, oleic acid, linolenic acid, linoleic acid, arachidic acid, arachidonic acid),
  (m) Fatty alcohols (e.g., cetearyl alcohol, cetyl alcohol, stearyl alcohol, oleyl alcohol),
  (n) Esters of fatty acids (e.g., esters of caproic acid, caprylic acid, capric acid, lauric acid, myristic acid, palmitic acid, palmitoleic acid, stearic acid, oleic acid, linolenic acid, linoleic acid, arachidic acid, arachidonic acid, with alcohols such as glycerol, propylene glycol, sorbitan, isopropyl alcohol, caproic alcohol, capryl alcohol, capric alcohol, lauryl alcohol, myristyl alcohol, cetearyl alcohol, cetyl alcohol, palmoleyl alcohol, stearyl alcohol, oleyl alcohol, linoyl alcohol, linolenyl alcohol, arachidyl alcohol, arachidonyl alcohol) such as isopropyl myristate, capryl stearate, isopropyl olivate, cetearyl olivate, cetearyl oleate, glyceryl caprylate, glyceryl stearate citrate, and sorbitan olivate), natural and synthetic triglycerides (e.g., di- or tri-glycerides of fatty acids, such as glyceryl caprate or caprylic/capric triglyceride),
  (o) Natural fats and oils (e.g., vegetable oil, coconut oil, sesame oil, avocado oil, corn oil, castor oil, shea butter, cocoa butter, soybean oil, sunflower oil, safflower oil, olive oil and tallow),
  (p) Waxes (e.g., cetearyl wax, beeswax, carnauba wax, lanolin wax, candelilla wax, and paraffin wax),
  (q) Thickeners (e.g., silicas, xanthan gum, guar gum, agar, alginates, carrageenan, gellan gum, pectins, and modified cellulose polymers, such as hydroxycellulose, hydroxypropyl cellulose, hydroxyethyl cellulose, hydroxybutyl cellulose, hydropropyl methylcellulose, hydroxyethyl propyl cellulose),
(r) Emulsifiers (e.g. polyethylene glycol esters, fatty alcohol polyglycol ethers, fatty acid polyglycol ethers, polyglycerol fatty acid esters, sorbitol, sorbitan, and mono- and di-fatty acid esters of sorbitan),
(s) Sunscreen actives (e.g., titanium dioxide, zinc oxide, and UV absorption inhibitors, such as octyl methoxy cinnamate, benzophenone-3, and methylene bis-benzotriazolyl tetramethyl butyl phenol),
(t) Vitamins (e.g., vitamin A, vitamin E, esters of vitamin A or vitamin E, such as vitamin E acetate and retinyl palmitate) or pro-vitamin derivatives thereof such as, for example, vitamin E acetate.

2.8 Any of Compositions 2 or 2.1-2.7, wherein the composition is a cream, lotion or gel for the skin (e.g., face, hands, feet, etc.).

2.9 Any of Compositions 2 or 2.1-2.8, further comprising inorganic salts, brighteners, perfumes, colorants, sequestering agents, opacifiers, pearlizers, chelating agents (e.g., EDTA), or any combination thereof.

2.10 Any of Compositions 2 or 2.1-2.9, wherein the composition is a cosmetic product, cosmetic-removal product, hair care product, shaving product (e.g., creams, gels and foams), skin care product or personal cleansing product (e.g., liquid soaps, foams, gels, and lotions)

2.11 Any of Compositions 2 or 2.1-2.10, further comprising natural biological extracts, such as essential oils or fragrances (e.g., Amyris oil, cedarwood oil, cocoa absolute, copaiba balsam, menthe oil pays, myrrh resin, patchouli oil, vanillin, vetiver oil, Aloe extract, lemon extract, orange extract, mandarin extract, and oil or extract of anise, clove, basil, aniseed, cinnamon, geranium, rose, mint, lavender, thyme, rosemary, citronella, cypress, eucalyptus, peppermint, and sandalwood).

2.12 Any of Compositions 2 or 2.1-2.11, further comprising water, e.g., from 5-90% water by weight of the composition, for example, 10%-80%, 15%-80%, 20%-80%, 25%-80%, 25%-75%, 30%-75%, 30-80%, 40%-70%, 50%-75%, 50%-70%, 50%-65%, or 60%-70%, or 65-70%, or about 65%, or about 66%, or about 67%, or about 68%.

2.13 Any of Compositions 2 or 2.1-2.12, wherein the pH of the composition is from 8-14, for example, from 8.0-12.0, or from 8.0-10.0.

In some embodiments, provided are novel biocide/antibacterial systems that are compatible in a soap mix surfactant base having a pH at or above about 8.0. The novel biocide system may include a single antibacterial agent or a hybrid of multiple antibacterial agents. The biocide system provides effective antibacterial properties against both gram-positive and gram-negative bacteria.

In some embodiments, the compositions herein are basic—i.e., have a pH above 7, and preferably from 8-14, for example, from 8.0-12.0, or from 8.0-10.0.

In some embodiments, the antibacterial agents include one or more of chloroxylenol, o-cymen-5-ol, and optionally phenoxyethanol. Chloroxylenol is also known as 4-chloro-3,5-dimethylphenol, or PCMX. O-cymen-5-ol is also known as 4-isopropyl-3-methylphenol or IPMP. In some embodiments, the novel biocide compositions of this disclosure include one of chloroxylenol, o-cymen-5-ol, and phenoxyethanol. In some embodiments, the novel biocide systems of this disclosure include combinations of the antibacterial agents, for example chloroxylenol and o-cymen-5-ol; or for example chloroxylenol, o-cymen-5-ol and phenoxyethanol; or for example o-cymen-5-ol and phenoxyethanol.

In some embodiments, the present compositions; e.g., the personal care compositions described above, include chloroxylenol in an amount of from about 0.01% to about 2% by weight of the composition, about 0.05% to about 1% by weight of the composition, about 0.1% to about 0.8% by weight of the composition, about 0.2% to about 0.6% by weight of the composition, or about 0.3%, or 0.5%, by weight of the composition. In some embodiments, the chloroxylenol is present in an amount of about 0.05%, about 0.10%, about 0.15%, about 0.20%, about 0.25%, about 0.30%, about 0.35%, about 0.40%, about 0.45%, about 0.50%, about 0.55%, about 0.60%, about 0.65%, about 0.70%, about 0.75%, about 0.80%, about 0.85%, about 0.90%, about 0.95%, or about 1.00% by weight of the composition.

In some embodiments, the compositions of the present invention include o-cymen-5-ol in an amount of from about 0.001% to about 5% by weight of the composition, about 0.01% to about 3% by weight of the composition, about 0.05% to about 0.5% by weight of the composition, or about 0.1% by weight of the composition. In some embodiments, the o-cymen-5-ol is present in an amount of about 0.01%, about 0.02%, about 0.03%, about 0.04%, about 0.05%, about 0.06%, about 0.07%, about 0.08%, about 0.09%, about 0.10%, about 0.11%, about 0.12%, about 0.13%, about 0.14%, about 0.15%, about 0.16%, about 0.17%, about 0.18%, about 0.19%, or about 0.20% by weight of the composition.

In some embodiments, the biocide composition includes phenoxyethanol. Preferably, the phenoxyethanol is present in an amount effective to produce an antibacterial effect, either alone or in combination with other components of the composition. In some embodiments, the phenoxyethanol is present in an amount of from about 0.01% to about 5% by weight of the composition, about 0.1% to about 2% by weight of the composition, or about 0.5% to about 1% by weight of the composition; for example from about 0.75% to about 1%, by weight of the composition.

In certain embodiments, the personal care composition is in the form of a cleansing liquid. In some embodiments, the cleansing liquid includes one or more fatty acid soaps. The fatty acid soap can be any neutralized fatty acid. Typical fatty acids used for soaps include, myristic acid, lauric acid, palmitic acid, stearic acids, and other fatty acids. Sources of fatty acids include coconut oil, palm oil, palm kernel oil, tallow, avocado, canola, corn, cottonseed, olive, hi-oleic sunflower, mid-oleic sunflower, sunflower, palm stearin, palm kernel olein, safflower, and babassu oils. The fatty acids can be neutralized with any base to form a soap. Typical bases include, but are not limited to, sodium hydroxide, potassium hydroxide, and triethanolamine. In some embodiments, the soap is a potassium soap. In some embodiments, the soap is a soap of lauric acid, myristic acid, and optionally a mixture of $C_{12-18}$ fatty acids.

In certain embodiments, the cleansing soap is in the form of a cleansing bar. The cleansing bar of the present disclosure includes at least one soap component. In certain embodiments the soap component is a hydrophilic soap chip (e.g., "a base component"). The term "soap" or "soap chip" is used herein in its popular sense, i.e., the alkali metal or alkanol ammonium salts of aliphatic alkane or alkene monocarboxylic acids.

Sodium, potassium, mono-, di- and tri-ethanol ammonium cations, or combinations thereof, are suitable for purposes of this invention. In general, sodium soaps are used in the compositions of the present disclosure, but from about 1% to about 25% of the soap may be ammonium, potassium, magnesium, calcium soaps or a mixture of these soaps. It is understood that the components of the cleansing bar as described above may be used in a cleansing liquid, and vice versa.

The compositions of the present disclosure can include one or more emollient compounds. Illustrative examples of such emollient components include mineral oils (e.g., paraffin oil, petroleum jelly oil), animal oils (e.g., fish oils and lanolin oil), vegetable oils (e.g., sweet almond oil, palm oil, avocado oil, olive oil, castor oil, cereal germ oil, canola oil, sunflower oil, soybean oil, and jojoba oil), triglycerides (e.g., caprylic/capric triglyceride), silicone oils (e.g., cyclomethicone), ester oils (e.g., butyl myristate, isopropyl myristate, cetyl myristate, isopropyl palmitate, isopropyl stearate, octyl stearate, isocearyl stearate), organic fatty alcohols (e.g., oleic alcohol, linolenic alcohol, linoleic alcohol, isostearyl alcohol, octyl dodecanol), and free fatty acids (e.g., linoleic acid, myristic acid, palmitic acid, stearic acid).

Illustrative examples of emulsifying agents include ethoxylated carboxylic acids, ethoxylated glycerides, glycol esters, monoglycerides, polyglyceryl esters, polyhydric alcohol esters and ethers, sorbitan/sorbitol esters, triesters of phosphoric acid, and ethoxylated fatty alcohols. Examples include glyceryl stearate, PEG-100 stearate, sorbitan stearate, PEG-40 stearate, polysorbate-20, polysorbate-60, polysorbate-80, and glyceryl oleate.

In some embodiments, the personal care compositions of the present disclosure further comprise one or surfactants, including anionic surfactants, zwitterionic amphoteric) surfactants, or nonionic surfactants, or mixtures thereof.

Anionic surfactants useful herein include the water-soluble salts of alkyl sulfates and alkyl ether sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium laurel ether sulfate (SUS), sodium lauryl sulfate and sodium coconut monoglyceride sulfonates are examples of anionic surfactants of this type. Other suitable anionic surfactants are sarcosinates, such as sodium lauroyl sarcosinate, taurates, sodium lauryl sulfoacetate, sodium lauroyl isethionate, sodium laureth carboxylate, and sodium dodecyl benzenesulfonate. Mixtures of anionic surfactants can also be employed.

Examples of nonionic surfactants that can be used in the present compositions include those that can broadly be defined as compounds produced by the condensation of alkylene oxide groups (hydrophilic in nature) with an organic hydrophobic compound which may be aliphatic or alkyl-aromatic in nature. Other examples of suitable nonionic surfactants include but are not limited to monoethanolamides, for example $C_{8-18}$ alkyl monoethanolamides, for example cocomonoethanolamide, lauramide monoethanolamide, and the like. Further examples of suitable nonionic surfactants include poloxamers (sold under trade name PLURONIC®), polyoxyethylene, polyoxyethylene sorbitan esters (sold under trade name TWEENS®), Polyoxyl 40 hydrogenated castor oil, fatty alcohol ethoxylates, polyethylene oxide condensates of alkyl phenols, products derived from the condensation of ethylene oxide with the reaction product of propylene oxide and ethylene diamine, ethylene oxide condensates of aliphatic alcohols, alkyl polyglycosides (for example, fatty alcohol ethers of polyglycosides, such as fatty alcohol ethers of polyglycosides, e.g., decyl, lauryl, capryl, caprylyl, myristyl, stearyl and other ethers of glucose and polyglucoside polymers, including mixed ethers such as capryl/caprylyl ($C_{8-10}$) glucoside, coca ($C_{8-16}$) glucoside, and lauryl ($C_{12-16}$) glucoside), long chain tertiary amine oxides, long chain tertiary phosphine oxides, long chain dialkyl sulfoxides, and mixtures of such materials.

Amphoteric surfactants, also known as zwitterionic surfactants, that can be used can be broadly described as derivatives of aliphatic secondary and tertiary amines in which the aliphatic radical can be a straight chain or branched and wherein one of the aliphatic substituents contains from 8 to 18 carbon atoms and one contains an anionic water-solubilizing group, e.g., carboxylate, sulfonate, sulfate, phosphate, or phosphonate. Other suitable amphoteric surfactants are betaines, specifically cocamidopropyl betaine. Mixtures of amphoteric surfactants can also be employed. Further examples of suitable amphoteric surfactants include sultaines, also known as sulfobetaines, and hydroxy sultaines, for example cocamidopropyl hydroxysultaine.

The personal care compositions of the present invention can also include one or more of a variety of optional ingredients, the selection of which can depend in part on the particular form of the composition, for example whether the composition is a solid (e.g., a cleansing bar) or a liquid (e.g., a liquid soap product). Non-limiting examples of such optional ingredients include skin conditioning agents, moisturizing agents, fragrance, coloring agents such as dyes and pigments, titanium dioxide, chelating agents such as EDTA, sunscreen active ingredients such as butyl methoxy benzoylmethane; antiaging compounds such as alpha hydroxy acids, beta hydroxy acids; preservatives such as hydantoins, imidazolines; polyols such as glycerol, sorbitol, propylene glycol and polyethylene glycols; antioxidants such as butylated hydroxytoluene (BHT); vitamins such as A, E, K and C; amino acids; essential oils and extracts thereof such as rosewood and jojoba.

In some embodiments, the personal care compositions of the disclosure (e.g. cleansing compositions) include fragrance in an amount of about 0.001% to about 2% by weight of the composition.

In some embodiments, the personal care compositions of the disclosure include pearlizers, such as titanium dioxide, in an amount of about 0.01% to 1% by weight.

In some embodiments, the personal care compositions of the disclosure include one or more pigments, such as chromium oxide green, in an amount of about 0.001% to about 1% by weight.

In some embodiments, the personal care compositions of the disclosure include one or more of inorganic salts, brighteners, perfumes, colorants, sequestering agents, opacifiers, chelating agents (e.g., EDTA), humectants (e.g., polyols, for example, glycerol), or any combination thereof.

In some embodiments, the personal care composition is in the form of a cleansing soap. In some embodiments, the cleansing soap includes free fatty acids to provide enhanced skin feel benefits, such as softer or smoother feeling skin. Suitable free fatty acids include those derived from tallow, coconut oil, palm oil and palm kernel oil.

In other embodiments, the present invention includes a method (Method 1) of cleansing a surface comprising providing a personal care composition as described above (e.g., any. Composition 1 and 1.1-1.17); and applying the composition to the surface.

The present disclosure provides additional exemplary embodiments, including:

1.1 Method 1, wherein the wherein the surface comprises skin.
1.2 Method 1 or 1.1, surface has a population of bacteria.
1.3 Method 1 or 1.1-1.2, wherein the composition is in the form of a liquid soap or a bar soap.

1.4 Method 1 or 1.1-1.3, wherein the composition is in the form of a liquid soap.

1.5 Method 1 or 1.3, wherein the composition is in the form of a bar soap.

In further embodiments, the present invention includes a method (Method 2) for reducing the population of bacteria on a skin surface, comprising contacting the skin surface with a personal care composition as described above (e.g., any Composition 1 and 1.1-1.17).

In other embodiments, the present invention includes a method (Method 3) for preparing an antibacterial cleansing composition comprising combining an effective amount of chloroxylenol (PCMX) and o-cymen-5-ol (IPMP), and optionally phenoxyethanol, with at least one surfactant.

In some embodiments, the present invention provides a personal care composition comprising an effective amount of an antibacterial component and a surfactant system; said antibacterial component selected from: phenoxyethanol; chloroxylenol (PCMX) and o-cymen-5-ol (IPMP); piroctone olamine; and combinations thereof. Other embodiments provide personal care compositions wherein the surfactant system comprises an anionic surfactant and a betaine-type surfactant in substantially similar amounts. Further embodiments provide personal care compositions wherein the composition is substantially free of chlorinated compounds.

Still further embodiments provide personal care compositions comprising phenoxyethanol in an amount of about 0.1% to about 5% by weight of the composition, about 0.5% to about 2% by weight of the composition, or about 0.75 to about 1% by weight of the composition. Other embodiments provide personal care compositions further comprising piroctone olamine in an amount of about 0.05% to about 0.5% by weight of the composition, or about 0.1% by weight of the composition.

The compositions herein can be prepared by procedures known in the art in general, the various components of the composition are combined with water and mixed to uniformity. Premixes, for example containing one or more components of the antibacterial component, can be employed to add several components simultaneously, for example where components are powders. Alternatively, the components of the composition can be added sequentially.

Exemplary embodiments of the present disclosure will be illustrated by reference to the following examples, which are included to exemplify, but not to limit the scope of the present invention.

EXAMPLES

Example 1

Table 1 (below) describes eight (8) compositions comprising chloroxylenol (PCMX) and o-cymen-5-ol (IPMP), phenoxyethanol (PE) or combinations thereof (Formulas I to VIII); and a comparative composition (Comp. Ex. I).

TABLE 1

| Ingredient | Comp. Ex. I | Formula I | Formula II | Formula III | Formula IV | Formula V | Formula VI | Formula VII | Formula VIII |
|---|---|---|---|---|---|---|---|---|---|
| EDTA-Tetrasodium Salt | 0.1470 | 0.1470 | 0.1470 | 0.1470 | 0.1470 | 0.1470 | 0.1470 | 0.1470 | 0.1470 |
| SLES 70% | 8.000 | 8.000 | 8.000 | 8.000 | 8.000 | 8.000 | 8.000 | 8.000 | 8.000 |
| Cocoamidopropyl Betaine | 8.450 | 8.450 | 8.450 | 8.450 | 8.450 | 8.450 | 8.450 | 8.450 | 8.450 |
| 47% Potassium Hydroxide Solution | 4.230 | 4.230 | 4.230 | 4.230 | 4.230 | 4.230 | 4.230 | 4.230 | 4.230 |
| Lauric Acid | 4.324 | 4.324 | 4.324 | 4.324 | 4.324 | 4.324 | 4.324 | 4.324 | 4.324 |
| C12-18 Fatty Acid Blend | 2.117 | 2.117 | 2.117 | 2.117 | 2.117 | 2.117 | 2.117 | 2.117 | 2.117 |
| Myristic Acid | 1.710 | 1.710 | 1.710 | 1.710 | 1.710 | 1.710 | 1.710 | 1.710 | 1.710 |
| Triclocarban | 0.1000 | — | — | — | — | — | — | — | — |
| Rhodasurf B7-B9 | 0.6167 | — | — | — | — | — | — | — | — |
| Promidium CO | 0.6167 | — | — | — | — | — | — | — | — |
| PCMX | — | 0.5000 | — | — | 0.2800 | 0.2800 | — | — | — |
| IPMP | — | — | 0.1000 | — | 0.1000 | 0.1000 | 0.1000 | — | — |
| Phenoxyethanol | — | — | — | 1.000 | 1.000 | — | 1.000 | 0.7500 | 0.7500 |
| Piroctone olamine | — | — | — | — | — | — | — | — | 0.1000 |
| Inactive Ingredients (water, fragrance, color, etc.) | Q.S. | Q.S. | Q.S. | Q.S. | Q.S. | Q.S. | Q.S. | Q.S. | Q.S. |

Three compositions comprising either PCMX, IPMP or PE (Formula I, Formula II, Formula III, Formula VII and Formula VIII) are prepared and tested for antibacterial efficacy. Formula I includes 0.5 wt. % of chloroxylenol (PCMX). Formula II includes 0.1 wt. % of o-cymen-5-ol (IPMP). Formula III and Formula VII include 1.0 wt. % and 0.75 wt. % of phyenoxyethanol, respectively. A comparative composition (Comp. Ex. I) is also tested to provide a basis of comparison for Formulas I, II, III, VII and VIII. Comp. Ex. I includes triclocarban.

Example 2

The Short Interval Kill Time SIKT) test is used to determine the in vitro short-term antimicrobial activity of several exemplary compositions of the present invention. This test assesses the reduction of a microbial population of test organisms after exposure to the test material in-vitro. Test materials are mixed with bacterial inoculum for a selected time interval, after which the test system is neutralized and surviving bacteria enumerated. The SIKT contact time is 1 minute. Soap samples or other viscous or solid samples must be diluted. Bacterial reduction compared to water is used as the basis for expressing activity.

*Staphylococcus aureus* and *Escherichia coli* are selected as the test organisms. *E. coli* is part of the normal flora of the gut. *S. aureus* is frequently found on the skin where perspiration is present, and is a common cause of skin infections such as abscesses, respiratory infections such as sinusitis, and food poisoning. *S. aureus* is a gram-positive bacterium and *E. coli* is a gram-negative bacterium. Formula 1, Formula 2, Formula 3, and Comp. Ex. I are subjected to the SIKT analysis. The results are shown in Table 2 (below).

TABLE 2

| Sample | Log Reduction |
| --- | --- |
| Comp. Ex. I | *S. aureus* = 5.96, *E. coli* = 7.11 |
| Formula I | *S. aureus* = 7.30, *E. coli* = 7.11 |
| Formula II | *S. aureus* = 6.52, *E. coli* = 7.11 |
| Formula III | *S. aureus* = 6.70, *E. coli* = 7.11 |
| Formula VII | *S. aureus* = 5.45, *E. coli* = 6.04 |
| Formula VIII | *S. aureus* = 5.01, *E. coli* = 6.21 |

The results for the SIKT test described in Table 2 (above) surprisingly show that Formula I, Formula II, and Formula III provide increased efficacy with respect to *S. aureus* kill rate, and a kill rate of *E. coli* similar to Comp. Ex. I. And, although the kill rates of Formula VII and Formula VIII against *S. aureus* and *E. coli* are less than the kill rates demonstrated by Comp. Ex. I against the same pathogens, given the combination of ingredients which comprise Formula VII and Formula VIII, these results are also unexpected.

The SIKT test is also carried out for formulations comprising combinations of multiple antibacterial agents. As shown below in Table 3, Comp. Ex, I is compared against a composition having PCMX, IPMP and Phenoxyethanol, a composition having PCMX and IPMP, and a composition having IPMP and Phenoxyethanol.

TABLE 3

| Sample | Inhibition % |
| --- | --- |
| Comp. Ex. I | *S. aureus* = 71%, *E. coli* = 49% |
| Formula IV | *S. aureus* = 69%, *E. coli* = 47% |
| Formula V | *S. aureus* = 68%, *E. coli* = 52% |
| Formula VI | *S. aureus* = 56%, *E. coli* = 57% |

The results described in Table 3 (above) show that the tested combinations effectively inhibit the proliferation of both *S. aureus* and *E. coli*. Surprisingly, the combinations of PCMX/IPMP/phenoxyethanol and PCMX/IPMP showed parity with Comp. Ex. I which includes triclocarban—a well-known antibacterial agent. These results indicate that various combinations of PCMX, IPMP and phenoxyethanol are effective in killing and inhibiting the proliferation of both gram-positive and gram-negative types of bacteria.

The invention has been described above with reference to illustrative Examples, but it is to be understood that the invention is not limited to the disclosed embodiments. Alterations and modifications that would occur to one of skill in the art upon reading the specification are also within the scope of the invention, which is defined in the appended claims

What is claimed is:

1. A personal care composition comprising:
   a) an antibacterial component comprising:
      i) chloroxylenol present in an amount of 0.01% to 2% by weight of the composition; and
      ii) o-cymen-5-ol present in an amount of 0.001% to 5% by weight of the composition;
   b) an effective amount of a surfactant system comprising:
      i) one or more fatty acid soaps;
      ii) an anionic surfactant; and
      iii) a betaine surfactant; and
   c) an effective amount of a chelating agent,
   wherein the composition has a pH of from 8-14, and the antibacterial component is free of Triclocarban, chlorinated compounds, Rhodasurf B7-B9, and Promidium CO.

2. The personal care composition of claim 1, wherein the chloroxylenol is present in an amount of 0.05% to 1% by weight of the composition; 0.1% to 0.8% by weight of the composition, 0.2% to 0.6% by weight of the composition, 0.2% to 0.4% by weight of the composition, or 0.3% by weight of the composition; or 0.5% by weight of the composition.

3. The personal care composition of claim 1, wherein the o-cymen-5-ol is present in an amount of 0.01% to 3% by weight of the composition, 0.05% to 0.5% by weight of the composition, or 0.1% by weight of the composition.

4. The personal care composition of claim 1, wherein the composition comprises 0.2% to 0.6% by weight of chloroxylenol and 0.05% to 0.5% by weight of o-cymen-5-ol.

5. The personal care composition of claim 1, wherein the anionic surfactant is selected from the group consisting of salts of alkyl sulfates and alkyl ether sulfates having from 8 to 20 carbon atoms in the alkyl radical and salts of sulfonated monoglycerides of fatty acids having from 8 to 20 carbon atoms.

6. The personal care composition of claim 1, wherein the betaine surfactant comprises cocamidopropyl betaine.

7. The personal care composition of claim 1, wherein said one or more fatty acid soaps comprises a potassium soap.

8. The personal care composition of claim 1, wherein the composition is in the form of a liquid soap or a bar soap.

9. The personal care composition according to claim 1, wherein the anionic surfactant and the betaine surfactant are in same amounts.

10. The personal care composition according to claim 1, wherein the composition comprises water in an amount of 50-75% by weight of the composition.

* * * * *